US007862775B2

(12) United States Patent
Swager et al.

(10) Patent No.: US 7,862,775 B2
(45) Date of Patent: Jan. 4, 2011

(54) DETERMINATION OF EXPLOSIVES INCLUDING RDX

(75) Inventors: Timothy M. Swager, Newton, MA (US); Trisha L. Andrew, Cambridge, MA (US); Samuel W. Thomas, III, Quincy, MA (US); Jean Bouffard, Lévis (CA)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/693,868

(22) Filed: Jan. 26, 2010

(65) Prior Publication Data

US 2010/0303672 A1 Dec. 2, 2010

Related U.S. Application Data

(62) Division of application No. 11/581,777, filed on Oct. 16, 2006, now Pat. No. 7,666,684.

(60) Provisional application No. 61/007,903, filed on Oct. 11, 2006.

(51) Int. Cl.
*G01N 21/00* (2006.01)

(52) U.S. Cl. ............... 422/82.05; 422/50; 422/68.1; 422/82.07; 436/106; 436/164; 436/172

(58) Field of Classification Search ............ 436/106, 436/164, 172; 422/82.05, 82.07, 68.1, 50
See application file for complete search history.

(56) References Cited

U.S. PATENT DOCUMENTS 5,306,642 A * 4/1994 Reagen et al. ............ 436/106
2006/0073607 A1 4/2006 Rose et al.

FOREIGN PATENT DOCUMENTS

EP 0586125 A 3/1994
WO WO 2006/009351 9/2006

OTHER PUBLICATIONS

Andrew et al., "A Fluorescence Turn-On Mechanism to Detect High Explosives RDX and PETN," *J. Am. Chem. Soc.* 2007, 129, 7254-7255.

(Continued)

*Primary Examiner*—Yelena G Gakh
*Assistant Examiner*—David Weisz
(74) *Attorney, Agent, or Firm*—Wolf, Greenfield & Sacks, P.C.

(57) ABSTRACT

The present invention provides sensors and methods for determination of an analyte. The analytes may be determined by monitoring, for example, a change in an optical signal of an emissive material upon exposure to an analyte. In some embodiments, the analyte and the emissive material may interact via a chemical reaction, or other chemical, biochemical or biological interaction (e.g., recognition), to form a new emissive species. In some cases, the present invention may be used for the detection of analytes such as explosives (e.g., RDX, PETN). Methods of the present invention may be advantageous in that the high sensitivity of luminescence (e.g., fluorescence) spectroscopy can allow for the reliable detection of small changes in luminescence intensity.

16 Claims, 10 Drawing Sheets

10

20

30

OTHER PUBLICATIONS

Beller et al., "Use of Liquid Chromatography/Tandem Mass Spectrometry to Detect Distinctive Indicators of In Situ RDX Transformation in Contaminated Groundwater," *Environ. Sci. Technol.* 2002, 36, 2060-2066.

Bhushan et al., "Biotransformation of Hexahydro-1,3,5-trinitro-1,3,5-triazine Catalyzed by NAD(P)H: Nitrate Oxidoreductase from *Aspergillus niger*," *Environ. Sci. Technol.* 2002, 36, 3104-3108.

Bruschini, C., "Commercial Systems for the Direct Detection of Explosives for Explosive Ordnance Disposal Tasks," *Subsurface Sensing Technologies and Applications* 2001, 2(3), 299-336.

Cheng et al., "Energetics of Multistep versus One-step Hydride Transfer Reactions of Reduced Nicotinamide Adenine Dinucleotide (NADH) Models with Organic Cations and p-Quinones," *J. Org. Chem.* 1998, 63, 6108-6114.

Cotte-Rodriguez et al., "Non-proximate detection of explosives and chemical warfare agent simulants by desorption electrospray ionization mass spectrometry," *Chem. Commun.* 2006, 2968-2970 (2006).

Fukuzumi et al., "Dehydrogenation vs Oxygenation in Photosensitized Oxidation of 9-Substituted 10-Methyl-9,10-dihydroacridine in the Presence of Scandium Ion," *J. Phys. Chem. A* 2002, 106, 1465-1472.

Fukuzumi et al., "Uphill Photooxidation of NADH Analogues by Hexyl Viologen Catalyzed by Zinc Porphyrin-Linked Fullerenes," *J. Phys. Chem. A* 2002, 106, 1903-1908.

Fukuzumi et al., "Selective One-Electron and Two-Electron Reduction of $C_{60}$ with NADH and NAD Dimer Analogues via Photoinduced Electron Transfer," *J. Am. Chem. Soc.* 1998, 120, 8060-8068.

Goldman et al., "A Hybrid Quantum Dot-Antibody Fragment fluorescence Resonance Energy Transfer-Based TNT Sensor," *J. Am. Chem. Soc.* 2005, 127, 6744-6751.

Haas et al., "Pathways of Radiative and Radiotionless Transitions in Europium (III) Solutions: Role of Solvents and Anions," *J. Phys. Chem.* 1971, 75(24), 3668-3677.

Kropp et al., "Luminescence and Energy Transfer in solutions of Rare-Earth Complexes. I. Enhancements of Fluorescence by Deuterium Substitution," *J. Chem. Phys.* 1965, 42(5), 1599-1608.

Kropp et al., "Enhancement of Fluorescence Yield of Rare-Earth Ions by Heavy Water," *J. Chem. Phys. Letters to Editor* 1963, 2769-2770.

McCormick et al., "Biodegradation of Hexahydro-1,3,5-Trinitro-1,2,5-Triazine," *Appl. Environ. Microbiol.* 1981, 42(5), 817-823.

McHugh et al., "The first controlled reduction of the high explosive RDX," *Chem. Commun.* 2002, 2514-1515.

McHugh et al., "Selective functionalisation of TNT for sensitive detection by SERRS," *Chem. Commun.* 2002, 580-581.

Meurer et al., Gas-phase reactions for selective detection of the explosives TNT and RDX, *Chem. Commun.* 2004, 40-41.

Ono et al., "1-Benzyl-1,4-dihydronicotinamide as a Reagent for Replacing Aliphatic Nitro Groups by Hydrogen: An Electron-Transfer Chain Reaction," *J. Am. Chem. Soc.* 1980, 102(8), 2851-2852.

Sheremata et al., "The Fate of the Cyclic Nitramine Explosive RDS in Natural Soil," *Environ. Sci. Technol.* 2001, 35, 1037-1040.

Sohn et al., "Detection of Nitroaromatic Explosives Based on Photoluminescent Polymers Containing Metalloles," *J. Am. Chem. Soc.* 2003, 125, 3821-3830.

Takats et al., "Direct, trace level detection of explosives on ambient surfaces by desorption electrospray ionization mass spectrometry," *Chem. Commun.* 2005, 1950-1952.

Tao et al., "Hierarchically Structured nanocomposite Films as Highly Sensitive Chemosensory Materials for TNT Detection," *Chem. Phys. Chem.* 2006, 7, 1902-1905.

Tao et al., "Metalloporphyrins as sensing elements for the rapid detection of trace TNT vapor," *J. Mater. Chem.* 2006, 16, 4521-4528.

Toal et al, "Polymer sensors for nitroaromatic explosives detection," *J. Mater. Chem.* 2006, 16, 2871-2883.

Wright et al., "Phosphorescence Lifetime of Benzene. An Intermolecular Heavy-Atom Effect, a Deuterium Effect, and a Temperature Effect," *J. Chem. Phys.* 1960, 934-935.

Yang et al., "Porous Shape Persistent Fluorescent Polymer Films: An Approach to TNT Sensory Materials," *J. Am. Chem. Soc.* 1998, 120, 5321-5322.

Yang et al., "Molecular recognition and self-assembled polymer films for vapor phase detection of explosives," *Talanta* 2001, 54, 439-445.

International Search Report and Written Opinion in International Application No. PCT/US2007/021701, mailed Oct. 31, 2009 (16 pages).

\* cited by examiner

DETERMINATION OF EXPLOSIVES INCLUDING RDX

RELATED APPLICATIONS

This application is a divisional of U.S. patent application Ser. No. 11/581,777, filed Oct. 16, 2006, which claims priority under 35 U.S.C. §119(e) to U.S. Provisional Application Ser. No. 61/007,903, filed Oct. 11, 2006, the contents of which applications are incorporated herein by reference in their entirety.

STATEMENT REGARDING FEDERALLY SPONSORED RESEARCH ON DEVELOPMENT

This invention was made with government support under grant number DAAD19-02-D-0002 awarded by the Army Research Office. The government has certain rights in this invention.

FIELD OF THE INVENTION

The present invention relates to devices and methods for determination of analytes, including explosives such as 2,4,6-hexahydro-1,3,5-triazinane (RDX) and pentaerythritol tetranitrate (PETN).

BACKGROUND OF THE INVENTION

Sensory devices based on amplified fluorescence quenching of solid-state conjugated polymer films can be highly sensitive, due to the amplification that arises from delocalized excitons sampling many potential binding sites within one excited state lifetime. Previous work has demonstrated highly sensitive detection schemes using these amplifying fluorescent polymers for a number of analytes in solution and vapor phase, as described in U.S. Publication No. 2003/0178607. For example, sensors for the ultratrace detection of high explosives such as 2,4,6-trinitrotoluene (TNT) have been shown to display high sensitivity comparable to that of trained canines. In many cases, the transduction mechanism is photoinduced charge transfer (PICT) from a polymer donor to a substantially planar, aromatic analyte that can bind to the conjugated polymer via pi-stacking interactions. For example, TNT is a planar, nitroaromatic molecule that can readily form a pi-complex with a conjugated polymer.

Although planar and/or aromatic compounds are often present in many explosives, present day security is in need of systems capable of matching comprehensive detection of a broader range of high explosives and toxins. For example, many military explosives compositions contain 2,4,6-hexahydro-1,3,5-triazinane (RDX) and/or pentaerythritol tetranitrate (PETN), both of which are non-planar, non-aromatic, explosive compounds.

Accordingly improved methods are needed.

SUMMARY OF THE INVENTION

The present invention relates to sensors comprising a compound comprising the structure,

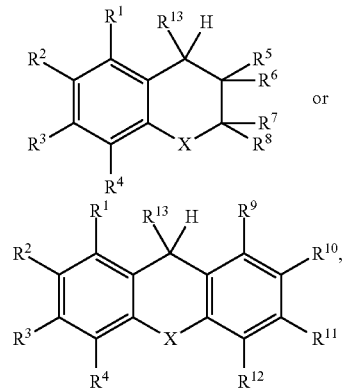

wherein each $R^1$-$R^{13}$ can be the same or different and can be alkyl, heteroalkyl, aryl, or heteroaryl, optionally substituted, or, at least two of $R^1$-$R^{13}$ are joined together to form a ring, optionally substituted; X is $CHR^{14}$ or $NR^{15}$; $R^{14}$, when present, is hydrogen, alkyl, heteroalkyl, aryl, or heteroaryl, optionally substituted; $R^{15}$, when present, is alkyl, heteroalkyl, aryl, or heteroaryl, optionally substituted, or $ML_y$, wherein M is a metal, L is a ligand, and y is at least 1; a source of energy applicable to the compound to cause an emission of radiation; and an emission detector positioned to detect the emission.

The present invention also provides methods for determination of an analyte comprising exposing a compound having a luminescence emission to a sample suspected of containing an analyte, wherein the analyte, if present, interacts with the compound to accept a hydride equivalent from the compound, causing a change in the luminescence emission of the compound; and determining the change in luminescence emission of the compound, thereby determining the analyte.

DETAILED DESCRIPTION

Figure 1A:
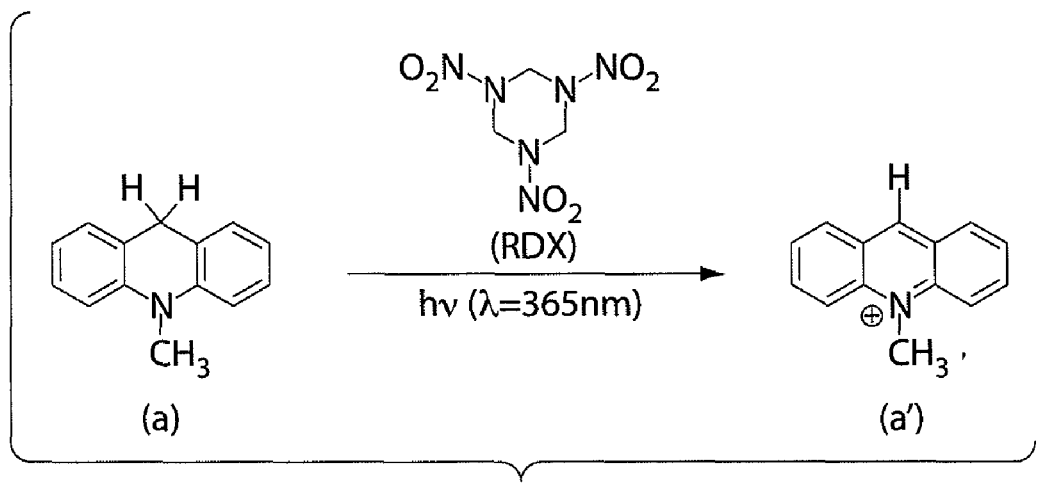
FIG. 1A shows a photochemical reaction wherein 9,10-dihydroacridine is converted to the acridinium salt in the presence of RDX.

The present invention generally relates to sensors and related methods, including determination of an analyte.

Analytes may be determined by monitoring, for example, a change in an optical signal of an emissive material upon exposure to an analyte. In some embodiments, the analyte and the emissive material may interact via a chemical reaction, or other chemical, biochemical or biological interaction (e.g., recognition), to form a new emissive species. The present invention may be useful in the detection of analytes such as explosives (e.g., RDX or PETN). Methods of the present invention may be advantageous in that the high sensitivity of luminescence (e.g., fluorescence) spectroscopy can allow for the reliable detection of small changes in luminescence intensity.

The present invention may be particularly advantageous in that analytes which do not readily interact with luminescent materials via, for example, pi-stacking interactions, may be determined. As used herein, "pi-stacking interactions" refer to cofacial interactions between pi-orbitals of conjugated species. Examples of such analytes include those which are, for example, non-planar, non-aromatic, and/or have relatively high reduction potentials (i.e., weak electron affinity). In some cases, the analyte may be an explosive. For example, 2,4,6-hexahydro-1,3,5-triazinane (RDX) may be characterized by a non-planar, three-dimensional structure, making it difficult for RDX to engage in pi-stacking interactions with luminescent materials having pi-conjugated moieties. Other non-planar, non-aromatic analytes may include 2,3-dimethyl-2,3-dinitrobutane (DMNB), 2,2-bis[(nitrooxy)-methyl]-1,3-propanediol dinitrate ester (pentaerythritol tetranitrate or PETN), 1,3,5,7-tetranitroperhydro-1,3,5,7-tetrazocine (HMX), nitroamines, nitroamides, nitroesters, other nitro- or nitrate-containing species, and the like. The present invention may also be advantageous since, in some cases, sensors and methods of the invention may generate a new signal in the presence of analyte (e.g., a "turn-on" detection mechanism), allowing for higher sensitivity in the determination of analytes.

Methods of the invention may comprise exposure of a compound having a luminescence emission to a sample suspected of containing an analyte (e.g., non-planar analytes, non-aromatic analytes), and, if present, the analyte interacts with the compound to cause a change in the emission of the compound. Determination of the change in the emission may then determine the analyte. In some cases, the change comprises a decrease or increase in luminescence intensity, and/or a change in the wavelength of the luminescence emission. As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction. In some embodiments, the interaction between the compound having a luminescence emission and the analyte may comprise a chemical reaction, such as a chemical reaction occurring upon exposure to electromagnetic radiation (e.g., photochemical reaction). The chemical reaction may produce a species having an emission (e.g., luminescence emission) that is different from the compound. In some cases, the species may have an emission that is separated from the emission of the compound by at least 30 nm or greater.

In some embodiments, the interaction between the compound and the analyte may comprise an electron-proton-electron transfer reaction, wherein the analyte accepts a hydride equivalent from the compound. As used herein, a "hydride equivalent" may refer to one or more species which, when combined together, form the net equivalent of a hydride ion (e.g., "H"). The hydride equivalent may be a hydride ion, or, may comprise a proton and two electrons, or any other combination of species which may form a hydride ion when combined. In some cases, upon exposure to electromagnetic radiation, the compound may donate or release a hydride equivalent in the presence of an analyte such that the compound becomes oxidized. The analyte may accept a single species from the compound, or the analyte may accept a combination of species from the compound, either simultaneously or sequentially. As used herein, an analyte "accepts" a species from the compound when the compound donates or otherwise transfers the species to the analyte, with or without formation of a bond (e.g., a covalent or non-covalent bond). In some cases, the analyte accepts a species from the compound via an electron transfer reaction and/or a proton transfer reaction. For example, the compound may transfer an electron to the analyte, such that a radical cation of the compound is formed.

In some embodiments, the electron-proton-electron transfer reaction comprises transfer of a proton and at least one electron (e.g., two electrons) from the compound to the analyte. The photochemical reaction may proceed in the presence of analyte upon exposure to a source of energy that may cause the compound to transfer an electron to the analyte (e.g., $\lambda$=365 nm). In some cases, the photochemical reaction may not proceed in the absence of an analyte, even upon exposure to the source of energy.

The compound may be any emissive material that can release or donate a hydride equivalent upon exposure to a source of energy, such as electromagnetic radiation. In some cases, the compound may form an emissive, aromatic moiety upon donation of a hydride equivalent to the analyte. The generation of the aromatic moiety may, in some cases, provide a driving force in the photochemical conversion of the compound. Examples of compounds suitable for use in the invention include, but are not limited to 1,4-dihydroquinolines, 9,10-dihydroacridines, 9,10-dihydroacenes (e.g., 9,10-dihydroanthracene), other hydride equivalent donors, metal complexes thereof, substituted derivatives thereof, and the like. In some cases, the compound may be substituted such that the compound has greater resistance to photo-oxidation by molecular oxygen, for example.

Figure 2:
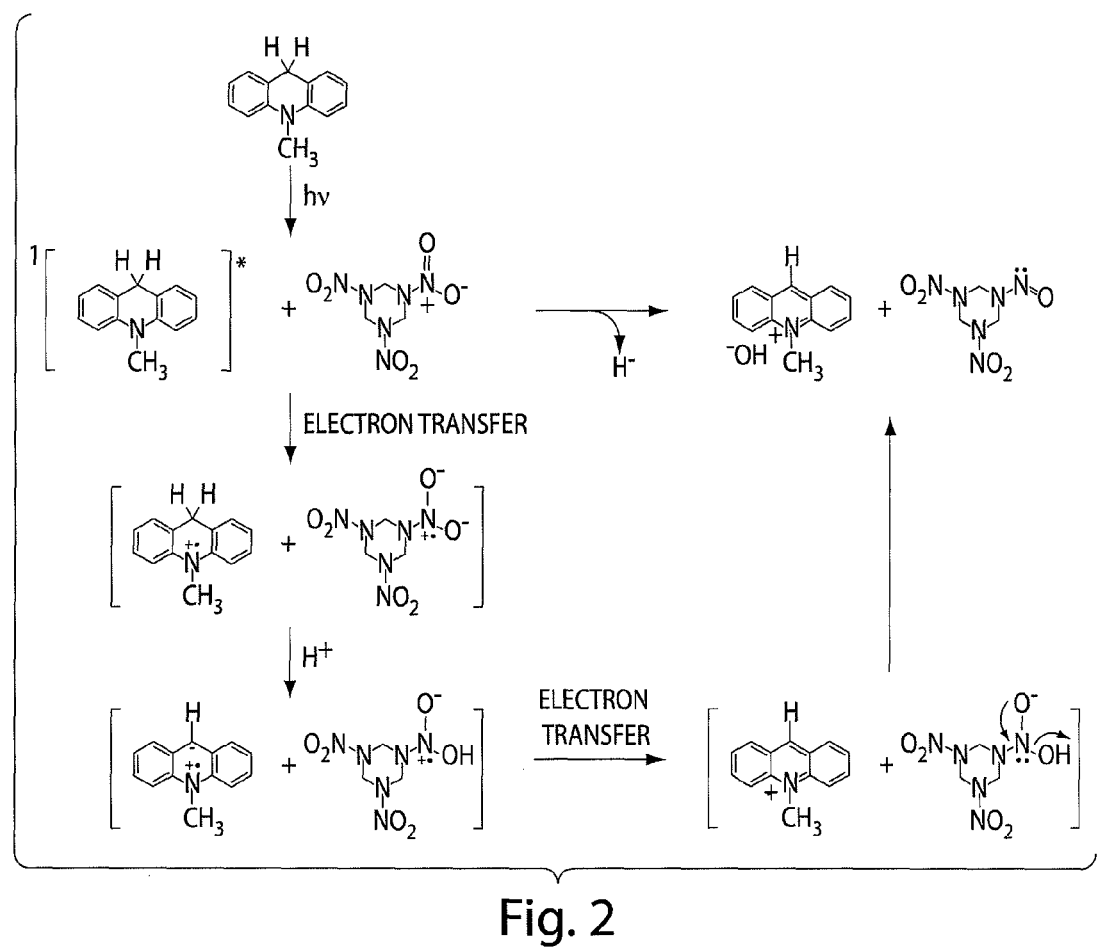
FIG. 2 shows a proposed mechanism for an electron-proton-electron transfer reaction to convert 9,10-dihydroacridine to the acridinium salt in the presence of RDX.
Figure 3:
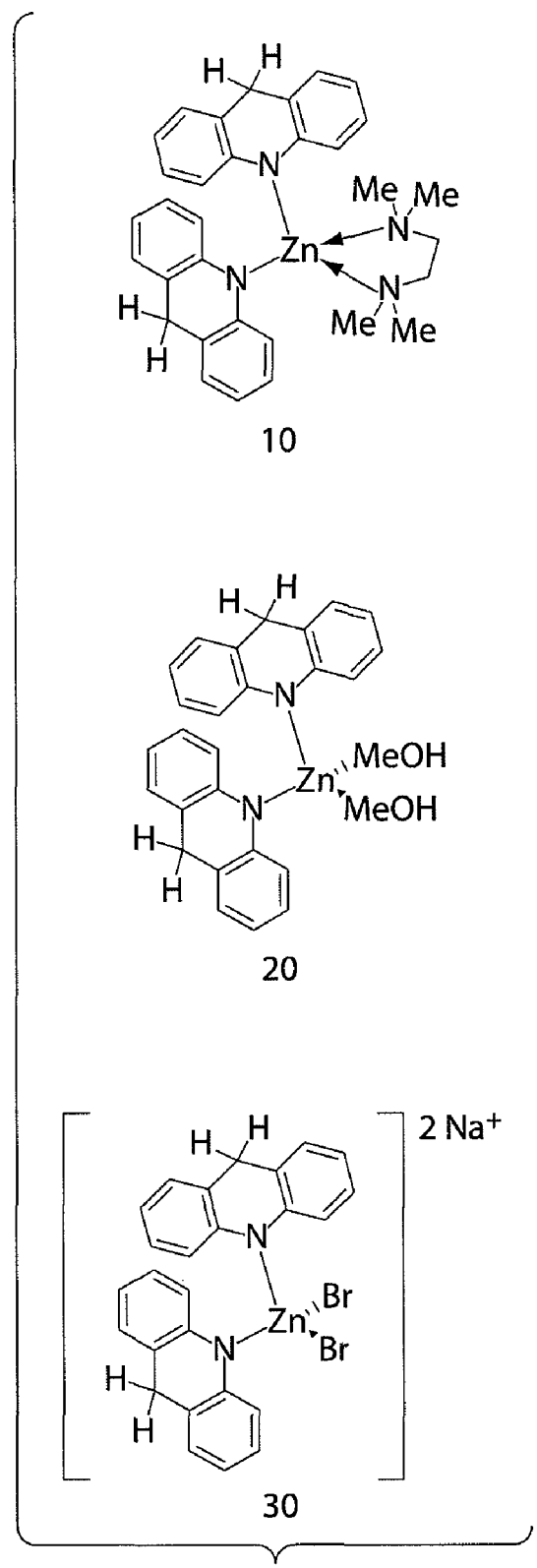
FIG. 3 shows examples of metal complexes comprising 9,10-dihydroacridine moieties.
Figure 9:
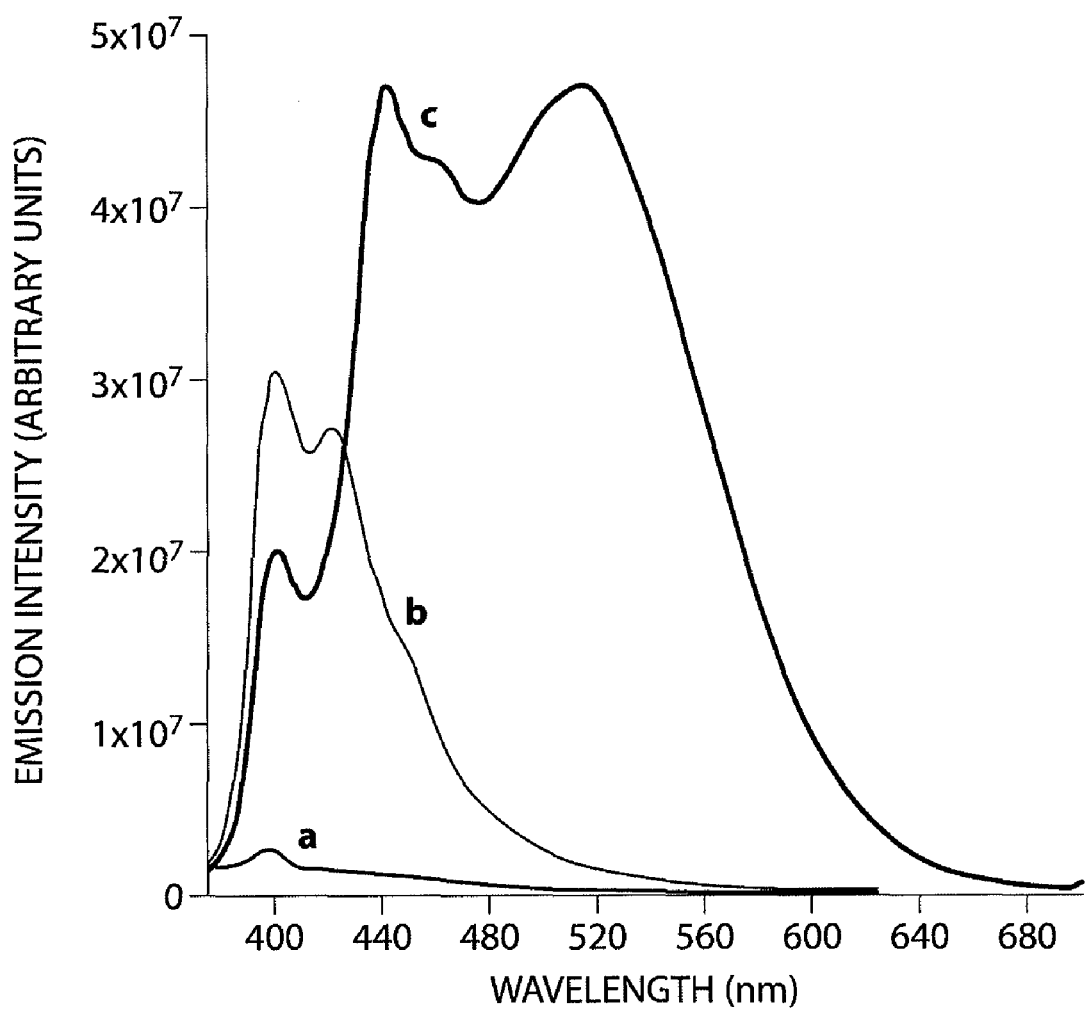
FIG. 9 shows the fluorescence emission spectra of (a) complex 20, (b) complex 20 upon irradiation with 365 nm light, and (c, c') the corresponding acridinium salt, formed upon exposure of complex 20 to RDX and irradiation with light (365 nm).
Figure 10:
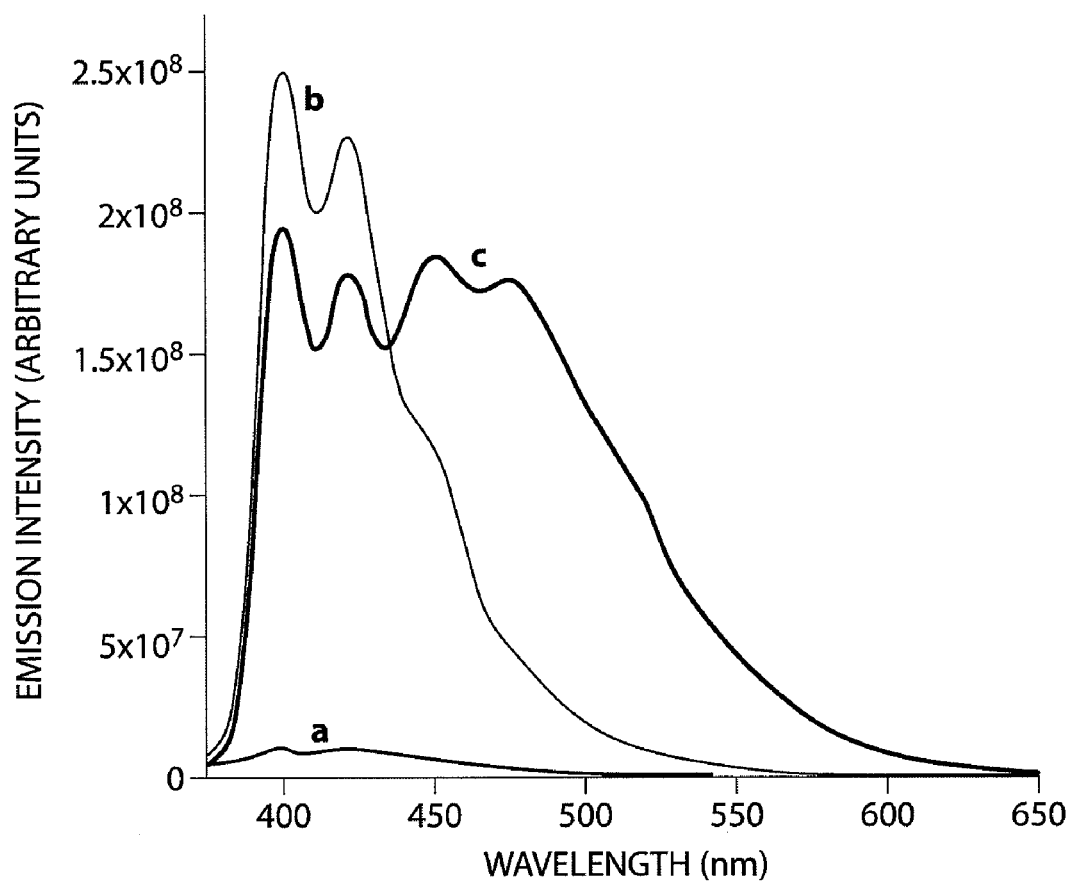
FIG. 10 shows the fluorescence emission spectra of (a) complex 30, (b) complex 30 upon irradiation with 365 nm light, and (c, c') the corresponding acridinium salt, formed upon exposure of complex 30 to RDX and irradiation with light (365 nm).

In the illustrative embodiment shown in FIG. 1A, methods of the invention may comprise the use of 9,10-dihydro-10-methylacridine (a). As shown in FIG. 1A, 9,10-dihydro-10-methylacridine (a) may be converted to the corresponding acridinium salt (a') via an electron-proton-electron transfer reaction upon exposure to RDX and irradiation with light ($\lambda$=365 nm). The emission of the resulting acridinium salt may determined, thereby determining the RDX. Without wishing to be bound by theory, FIG. 2 shows a proposed mechanism for an electron-proton-electron transfer reaction between 9,10-dihydro-10-methylacridine and RDX. Upon exposure to electromagnetic radiation, 9,10-dihydro-10-methylacridine, in an excited-state, may transfer a first electron to an RDX molecule to form the corresponding acridine radical cation, which may then transfer a proton to the RDX molecule. Transfer of a second electron from the acridine compound to the RDX molecule may produce an aromatic, acridinium salt.

Figure 1B:
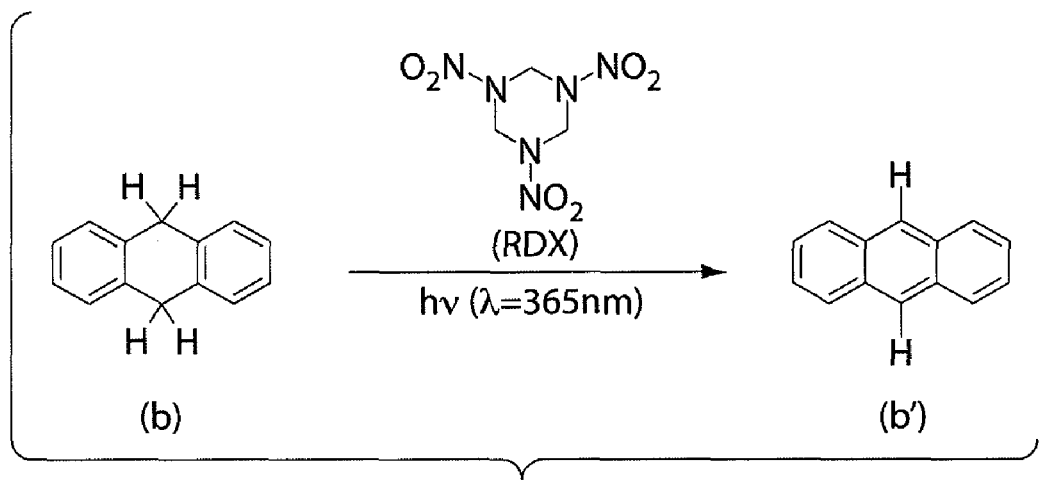
FIG. 1B shows a photochemical reaction wherein 9,10-dihydroanthracene is converted to anthracene in the presence of RDX.

FIG. 1B shows another embodiment using 9,10-dihydroanthracene (b) as the emissive compound, wherein 9,10-dihydroanthracene (b) may be converted to anthracene (b') via an electron-proton-electron transfer reaction upon exposure to RDX and irradiation with light ($\lambda$=365 nm). The emission of the resulting anthracene may determined, thereby determining the RDX. Other photochemical processes and reactions are known in the art and may be incorporated into the present invention. For example, in another illustrative embodiment, diaryl hydrazines such as N,N'-diphenyl hydrazine may be utilized, wherein N,N'-diphenyl hydrazine may interact with an analyte (e.g., RDX) in the presence of electromagnetic radiation to form azobenzene via a photochemical reaction. Those skilled in the art would readily recognize other photochemical systems which may be incorporated within the scope of the invention.

In some embodiments, the analyte may be determined in conditions wherein oxygen is present. In some embodiments, the analyte may be determined in substantially oxygen-free conditions. For example, in some cases, the compound may be readily oxidized by molecular oxygen during irradiation, thus leading to undesired changes in the luminescence emission of the compound. Thus, to reduce the oxidation of the compound by Molecular oxygen, the compound and sample may be placed in an environment wherein oxygen has been substantially removed, via nitrogen or argon purging, for example.

In some embodiments, the interaction between the compound and the analyte may further comprise, for example, energy transfer (e.g., photoinduced charge transfer, fluorescence resonance energy transfer), electrostatic interactions, binding interactions, redox reactions (e.g., reduction, oxidation), other chemical reactions, and the like. In some cases, the analyte may be an electron acceptor and the compound may be an electron donor or a hydride equivalent donor, as described herein. In some cases, the analyte may be an electron donor or a hydride equivalent donor and the compound may be an electron acceptor.

In some cases, methods of the invention comprise determining a change in the wavelength of an emission signal. For example, the interaction between the analyte and the compound may cause a shift in the wavelength of the luminescence intensity of the compound. That is, in the absence of analyte, the compound may have a first emission upon exposure to electromagnetic radiation, and, upon exposure to an analyte, the analyte may interact with at least a portion of the compound such that a second emission signal is generated at a different wavelength. The difference in the wavelengths of the first emission and the second emission may be at least 30 nm, or, in some embodiments, at least 50 nm, at least 75 nm, at least 100 nm, or at least 150 nm. The wavelength of an emission signal refers to the wavelength at which the peak maximum of the emission signal occurs in an emission spectrum. The emission signal may be a particular peak having the largest intensity in an emission spectrum (e.g. a fluorescence spectrum), or, alternatively, the emission signal may be a peak in an emission spectrum that has at least a defined maximum, but has a smaller intensity relative to other peaks in the emission spectrum. In some cases, upon exposure to the analyte, the second emission signal may be generated at a wavelength having substantially no emission signal in the absence of analyte (e.g., a "turn-on" detection mechanism).

In some embodiments, methods of the invention comprise determining a change in the luminescence intensity of an emission signal. The change in luminescence intensity may occur for an emission signal with substantially no shift in the wavelength of the luminescence (e.g., emission), wherein the intensity of the emission signal changes but the wavelength remains essentially unchanged. In other embodiments, the change in luminescence intensity may occur for an emission signal in combination with a shift in the wavelength of the luminescence (e.g., emission). For example, an emission signal may simultaneously undergo a shift in wavelength in addition to an increase or decrease in luminescence intensity. In another embodiment, the change may comprise two emission signals occurring at two different wavelengths, wherein each of the two emission signals undergoes a change in luminescence intensity. In some cases, the two emission signals may undergo changes in luminescence intensity independent of one another. In some cases, the two emission signals may undergo changes in luminescence intensity, wherein the two emission signals are associated with one another, for example, via an energy transfer mechanism, as described more fully below.

Methods of the present invention may comprise determining a change in luminescence intensity in combination with a change in the luminescence wavelength, upon exposure of the compound to an analyte. For example, the relative luminescence intensities of a first emission signal and a second emission signal associated with the first emission signal may be modulated using the methods described herein. In some cases, the first emission signal and the second emission signal may be associated with (e.g., interact with) one another via an energy transfer mechanism, such as fluorescence resonance energy transfer, for example. The term "fluorescence resonance energy transfer" or "FRET" is known in the art and refers to the transfer of excitation energy from an excited state species (i.e., FRET donor) to an acceptor species (i.e., FRET acceptor), wherein an emission is observed from the acceptor species.

In one embodiment, a first luminescent species may act as FRET donor and a second luminescent species may act as a FRET acceptor, wherein the first portion and the second portion each have different emission wavelengths. The first luminescent species may be associated with a quenching molecule and exist in a "quenched" state, wherein, upon exposure of the first portion to electromagnetic radiation, the quenching molecule absorbs the excitation energy and substantially no emission is observed. Upon exposure to an analyte, the analyte may interact with the first luminescent species and/or quenching molecule to "un-quench" the first luminescent species. As a result, exposure of the first luminescent species to electromagnetic radiation produces an excited-state, wherein the first luminescent species may transfer excitation energy to the second luminescent species, and emission signal from the second luminescent species is observed.

In some cases, the emission may also be visible by sight, e.g., the compound may emit visible light. This may allow for the determination of analytes via a colorimetric change. For example, the compound, in the absence of analyte, may have a first color, and, upon exposure to an analyte and irradiation by a source of energy, the compound may have a second color, wherein the change in color may determine the analyte.

The present invention also relates to sensors for the determination of analytes, wherein the sensors comprise compounds capable of releasing a hydride equivalent upon exposure to an analyte, as described herein. The compound may be in solution or in solid form. For example, the sensor may further comprise a solid support material, wherein the compound is dispersed within the support material. In some cases, the support material may be a polymer, such as poly(methyl methacrylate). The compound may be attached to the support material via covalent bonds or non-covalent bonds. In some embodiments, the compound may be non-covalently dispersed within the support material. In some cases, the solution or support material may comprise at least 1 wt % of compound, or, in some embodiments, at least 5 wt % of compound, at least 10 wt % of compound, at least 25 wt % of compound. In one embodiments, the solution or support material comprises 10 wt % of compound.

The sensor may further comprise at least one source of energy applicable to the compound. In some cases, a first source of energy may cause an emission of radiation from the compound and a second source of energy may cause the compound to transfer an electron to an analyte, i.e., in an electron-proton-electron transfer reaction, wherein the first source of energy and the second source of energy are different. In some cases, a single source of energy may cause an emission of radiation from the compound and may cause the compound to transfer an electron to an analyte. The source of energy may be an electric, magnetic, optical, acoustic, electromagnetic, or mechanical field. In some embodiments, the source of energy is electromagnetic radiation. The sensor may further comprise an emission detector positioned to detect the emission. The source of energy can be provided in combination with the compound and/or sensor in a variety of ways, such as being integrally and/or functionally connected to the compound/sensor (for example, by providing a compartment or other assembly supporting both the compound/sensor and the energy source), or in combination such that the compound/sensor and energy source can be used together (e.g., packaged together, or otherwise provided together and with the ability to arrange each, with respect to the other, for use as described herein). The emission detector can be provided in combination with the compound and/or sensor, in a manner as described above with respect to the energy source. Where the energy source and emission detector are both provided in combination with the compound/sensor, they can be provided in essentially identical or similar structural relation to the compound/sensor (e.g., both attached to a common housing or framework, to which the compound/sensor is also attached), or their relationship to the compound/sensor can differ.

In some embodiments, sensors of the invention may comprise an inlet for intake of a sample (e.g., vapor sample, solution sample), a sample cell comprising the compound, the sample cell constructed and arranged to receive the sample, and a detection mechanism in optical communication with the sample cell. Systems such as this may be useful in the determination of, for example, explosives such as RDX. As used herein, a sample cell "constructed and arranged" refers to a sample cell provided in a manner to direct the passage of a sample, such as a sample comprising RDX, from the inlet into the sample cell, such that the vapor sample contacts the compound. "Optical communication" may refer to the ability of the detection mechanism to receive and detect an optical signal (e.g., light emission) from the sample cell.

Methods for synthesizing sensors as described herein may comprise forming a fluid mixture comprising the compound and a support material or support material precursor, and solidifying the fluid mixture to produce a solid composition that is emissive upon exposure to a source of energy, such as electromagnetic radiation. In certain cases, forming the fluid mixture may comprise providing the support material or support material precursor as a fluid, and dissolving or suspending the compound in the fluid support material precursor. In some embodiments, forming the fluid mixture may comprise providing the support material as a solid, and suspending (i.e., immersing) the support material in the fluid mixture.

In some embodiments, forming the fluid mixture may comprise dissolving or suspending the compound and support material or support material precursor in an auxiliary fluid. In some embodiments, the auxiliary fluid is a solvent, such that forming the fluid mixture comprises dissolving the compound and support material or support material precursor in the solvent. Optionally, a catalyst, acid, base, buffer, and/or other additives (e.g., plasticizers, etc.) may be added to the fluid mixture. Solidification of the fluid mixture may comprise, in cases where a solvent is employed as an auxiliary fluid, removal of a solvent by, for example, evaporation or filtration. Solidification of the fluid mixture may also comprise, in cases where the support material precursor is provided as a fluid, conversion of the support material precursor to a support material (e.g., a solid support material).

As used herein, an emitted radiation or "emission" may be luminescence emission, in which "luminescence" is defined as an emission of ultraviolet or visible radiation. Specific types of luminescence include fluorescence, in which a time interval between absorption and emission of visible radiation ranges from $10^{-12}$ to $10^{-7}$ s, phosphorescence, other types of luminescence, and the like. For example, the emission may be "chemiluminescence," which refers to emission of radiation due to a chemical reaction, or "electrochemiluminescence," which refers to emission of radiation due to electrochemical reactions. In some cases, the emission may be fluorescence emission.

As described herein, compounds suitable for use in sensors and methods of the invention include emissive compound which are capable of donating or releasing a hydride equivalent upon exposure to an analyte and a source of energy, such as electromagnetic radiation. In some embodiments, the compound may form an aromatic moiety upon release of the hydride equivalent. The compound may also be capable of transferring an electron to an analyte upon exposure to a source of energy, such as electromagnetic radiation.

In some cases, the compound may comprise the structure,

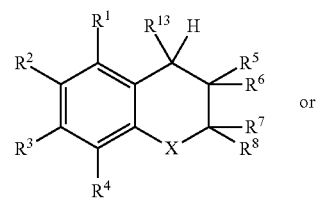 or

-continued

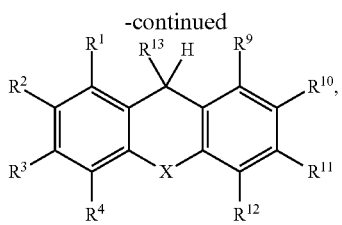

wherein each $R^1$-$R^{13}$ can be the same or different and can be alkyl, heteroalkyl, aryl, or heteroaryl, optionally substituted, or, at least two of $R^1$-$R^{13}$ are joined together to form a ring, optionally substituted; X is $CHR^{14}$ or $NR^{15}$; $R^{14}$, when present, is hydrogen, alkyl, heteroalkyl, aryl, or heteroaryl, optionally substituted; $R^{15}$, when present, is alkyl, heteroalkyl, aryl, or heteroaryl, optionally substituted, or $ML_y$, wherein M is a metal, L is a ligand, and y is at least 1. The ligand may be any moiety capable of coordinating a metal center, such as halide, hydroxy, amine, a carbonyl group, alkyl, heteroalkyl, aryl, heteroaryl, or substituted derivatives thereof, or multidentate ligands, such as bidentate ligands. In some cases, $R^{13}$ is hydrogen. In some embodiments, at least two of $R^1$-$R^{13}$ are joined together to form a cycloalkyl, heterocycloalkyl, aryl, or heteroaryl ring, or substituted derivative thereof. For example, at least two of $R^1$-$R^4$ or $R^9$-$R^{12}$ may be joined together to form an aryl ring, such than the compound comprises a polycyclic aromatic moiety, including linear (e.g., anthracene, pentacene) or non-linear (e.g., phenanthrene, perylene, etc.) polycyclic aromatic moieties. In some embodiments, the compound comprises a 9,10-dihydroacridine moiety, a dihydroacene moiety, or a substituted derivative thereof.

In one embodiment, the compound has the structure,

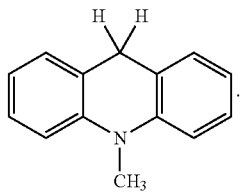

In another embodiment, the compound has the structure,

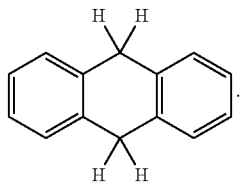

In another embodiment, the compound has the structure,

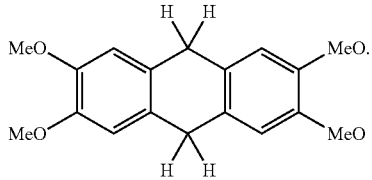

In some cases, the compound may a metal complex, wherein X is $NR^{15}$ and $R^{15}$ is $ML_y$. In some cases, the M is Co or Zn. In some cases, M is Zn. In some embodiments, the metal complex may comprise at least two ligands capable of interacting with an analyte as described herein.

In some embodiments, the compound has the structure,

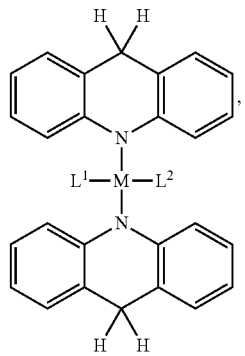

wherein M is a metal, and $L^1$ and $L^2$ can be the same or different and are halide, hydroxy, amine, a carbonyl group, alkyl, heteroalkyl, aryl, heteroaryl, or substituted derivatives thereof, or $L^1$ and $L^2$ are joined together to form a bidentate ligand. In some embodiments, M is Zn and $L^1$ and $L^2$ are halide, methanol, or $L^1$ and $L^2$ are joined together to form ethylenediamine or a substituted derivative thereof. In some embodiments, $L^1$ and $L^2$ are joined together to form a ligand having the structure,

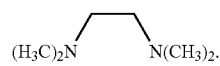

The properties of the compounds may be tuned based on the substitution of the various compounds. Those skilled in the art would recognize which types of functional groups would afford a particular, desired property, such as a particular emission wavelength or a resistance to photo-oxidation by molecular oxygen. For example, the compound may be substituted with electron-poor groups, such as acyl, carboxyl, cyano, nitro, sulfonate, or the like, such that the compound exhibits fluorescence emission at shorter wavelengths. In other embodiments, the compound may be substituted with electron-rich groups, such as amino, hydroxy, alkoxy (e.g., methoxy), acylamino, acyloxy, alkyl, halide, and the like, such that the monomer exhibits fluorescence emission at longer wavelengths. In some embodiments, the compound may tailored to advantageously have a large Stokes shift, wherein the fluorescence spectrum is observed at a substantially longer wavelength than the excitation spectrum. In some embodiments, the compound may be substituted with functional groups, such as electron-rich groups, which may enhance the ability of the compound to donate or transfer an electron or hydride equivalent to an analyte. In some cases, the compound may comprise a functional group which enhances resistance of the compound to photo-oxidation by molecular oxygen. For example, the compound may be a metal complex comprising a zinc metal center.

Metals suitable for use in the invention may be metal centers which are stable and resistant to, for example, photo-oxidation. The metal may be selected from those that have usually at least one, two, three, four, five, six, seven coordination sites or more. In some embodiments, the compositions and methods of the invention may be used with a wide range of metal ions, including light metals (Groups 1 and 2 of the Periodic Table), transition metals (Groups 3-12 of the Periodic Table), posttransition metals, metals of the lanthanide series and metals of the actinide series. As used herein, Group 3 of the Periodic Table refers to the group containing Sc, Y, La, and Ac; Group 4 refers to the group containing Ti, Zr, Hf, etc. In one embodiment, the metal is a Group 9 metal (e.g., Co, Rh, Ir, etc.). In one embodiment, the metal is a Group 12 metal (e.g., Zn, Cd, Hg). In a particular embodiment, the metal is Zn. In a particular embodiment, the metal is Co.

As described herein, the compound may be contained in solution or dispersed within a support material. The compound may be dissolved or suspended in any fluid which does not react with the analyte, compound, or intermediates or products thereof, or does not otherwise interfere with the determination of the analyte. The fluid may be aqueous, organic, or combinations thereof. In some embodiments, the fluid is an organic solvent, including polar and non-polar solvents. In one embodiment, the compound may be contained in acetonitrile.

The support material may be any material capable of supporting (e.g., containing) the compounds as described herein. For example, the support material may be selected to have a particular surface area wherein the support material may absorb or otherwise contact a sufficient amount of analyte (e.g., RDX) to allow interaction between the analyte and, for example, the compound. In some embodiments, the support material has a high surface area. In some cases, the support material has a surface area of at least 50 mm$^2$, at least 100 mm$^2$, at least 200 mm$^2$, at least 300 mm$^2$, at least 400 mm$^2$, or, more preferably, at least 500 mm$^2$.

In some embodiments, the support material may have a low background signal, substantially no background signal, or a background signal which does not substantially interfere with the signal generated by the compound, either in the presence or in the absence of analyte. That is, the support material may be optically transparent relative to the emissive compound and/or photochemical products thereof. The support material may be soluble, swellable, or otherwise have sufficient permeability in systems of the invention to permit, for example, intercalation of compounds as described herein, and other components within the support material. In one embodiment, the support material may be hydrophobic, such that a hydrophobic solution containing the compound may diffuse or permeate the support material. In another embodiment, the support material may form a homogeneous solution with the compound. Additionally, the support material may preferably permit efficient contact between the sample (e.g., analyte) to be determined and the compound. For example, in one embodiment, a vapor or solution comprising an analyte may permeate the support material to interact with the compound via a photochemical reaction. The permeability of certain support materials described herein are known in the art, allowing for the selection of a particular support material having a desired diffusion. The choice of support material may also affect the intensity and duration of light emission from the system.

Examples of support materials include polymers, copolymers, gels, and other solid adsorbent materials. In some embodiments, the support material may have a shape or be formed into a shape (for example, by casting, molding, extruding, and the like). In some cases, the support material may be a film. In some embodiments, the support material may be a polymer. Examples include poly(methyl methacrylate), polyethylene, polypropylene, poly(vinyl chloride), poly(vinyl benzoate), poly(vinyl acetate), cellulose, corn starch, poly(vinyl pyrrolidinone)s, polyacrylamides, epoxys, silicones, poly(vinyl butyral)s, polyurethanes, nylons, polacetals, polycarbonates, polyesters and polyethers, polybutadiene copolymers, crosslinked polymers, combinations thereof, and the like. In some cases, the polymer may be a conjugated polymer, such as polyarylenes, polyarylene vinylenes, polyarylene ethynylenes and ladder polymers, i.e. polymers having a backbone that can only be severed by breaking two bonds. In one embodiment, the polymer is poly(methylmethacrylate), poly(vinylpyrrolidinone), or poly(4-vinylpyridine). In one embodiment, the polymer is poly(methylmethacrylate). In one embodiment, the polymer is poly(vinylpyrrolidinone).

The combination of support material and solvent may have a desired diffusion rate, controlling the intensity and duration of light emission. The permeability of a particular polymer is known in the art.

Sensors comprising compounds dispersed (e.g., non-covalently dispersed) within a support material are described herein by way of example only, and it should be understood that, in some cases, other configurations of compounds and support materials may be encompassed within the scope of the invention. For example, the compound (e.g., hydride equivalent donor) may be covalently bonded to the support material, such as a polymer. In some cases, the compound may be covalently bonded to a polymer backbone via a pendant side group. In some cases, the compound may be positioned within a polymer backbone.

The analyte may be any chemical or biological species capable of accepting an electron from the compounds as described herein. In some cases, the analyte is a non-aromatic, nitro-containing species. In some cases, the analyte may be an explosive. For example, the analyte may be RDX, DMNB, PETN, HMX, other nitro- or nitrate-containing species (e.g., nitroamines), and the like. In some embodiments, the analyte is RDX. In some embodiments, the analyte is PETN.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "heteroalkyl" is given its ordinary meaning in the art and refers to alkyl groups as described herein in which one or more atoms is a heteroatom (e.g., oxygen, nitrogen, sulfur, and the like).

The term "aryl" is given its ordinary meaning in the art and refers to single-ring aromatic groups such as, for example, 5-, 6- and 7-membered single-ring aromatic groups. The term "heteroaryl" is given its ordinary meaning in the art and refers to aryl groups as described herein in which one or more atoms is a heteroatom (e.g., oxygen, nitrogen, sulfur, and the like). Examples of aryl and heteroaryl groups include, but are not limited to, benzene, pyrrole, furan, thiophene, imidazole, oxazole, thiazole, triazole, pyrazole, pyridine, pyrazine, pyridazine and pyrimidine, and the like.

The term "polycyclic" refers to ring systems having two or more cyclic rings in which two or more atoms are common to two adjoining rings (e.g., the rings are "fused rings").

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted benzene" must still comprise the benzene moiety and can not be modified by substitution, in this definition, to become, e.g., a cyclohexyl group. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, lower alkyl, lower aryl, lower aralkyl, lower cyclic alkyl, lower heterocycloalkyl, hydroxy, lower alkoxy, lower aryloxy, perhaloalkoxy, aralkoxy, lower heteroaryl, lower heteroaryloxy, lower heteroarylalkyl, lower heteroaralkoxy, azido, amino, halogen, lower alkylthio, oxo, lower acylalkyl, lower carboxy esters, carboxyl, -carboxamido, nitro, lower acyloxy, lower aminoalkyl, lower alkylaminoaryl, lower alkylaryl, lower alkylaminoalkyl, lower alkoxyaryl, lower arylamino, lower aralkylamino, lower alkylsulfonyl, lower-carboxamidoalkylaryl, lower -carboxamidoaryl, lower hydroxyalkyl, lower haloalkyl, lower alkylaminoalkylcarboxy-, lower aminocarboxamidoalkyl-, cyano, lower alkoxyalkyl, lower perhaloalkyl, lower arylalkyloxyalkyl, and the like.

EXAMPLES

The compounds described herein were synthesized according to methods known in the art. Photochemical irradiation was performed with a 500 W Hg arc lamp ($\lambda$=365 nm, 405 nm) fitted with a 0.5 OD Neutral Density Filter. Exposure times varied from 30 to 50 seconds. UV/vis spectra were recorded on an Agilent 8453 diode-array spectrophotometer and corrected for background signal with either a solvent-filled cuvette (for solution measurements) or a clean glass cover slip (for thin film measurements). Emission spectra were acquired on a SPEX Fluorolog-τ3 fluorometer (model FL-321, 450 W Xenon lamp) using either right angle detection (solution measurements) or front face detection (thin film measurements).

Example 1

Figure 4:
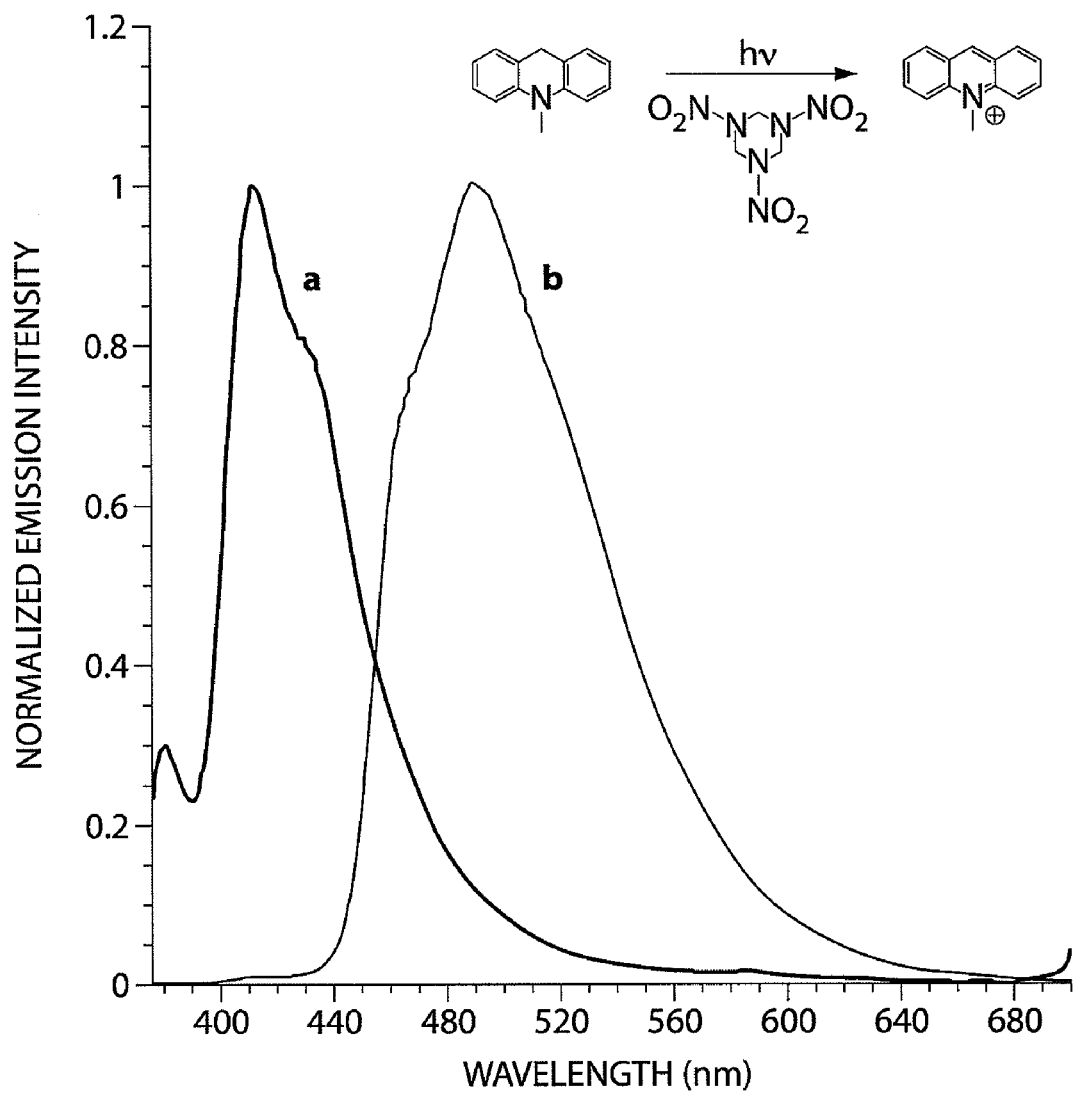
FIG. 4 shows the fluorescence emission spectra of (a) 9,10-dihydro-10-methylacridine and (b) the corresponding acridinium salt, formed upon exposure of 9,10-dihydroacridine to RDX and electromagnetic radiation.
Figure 5:
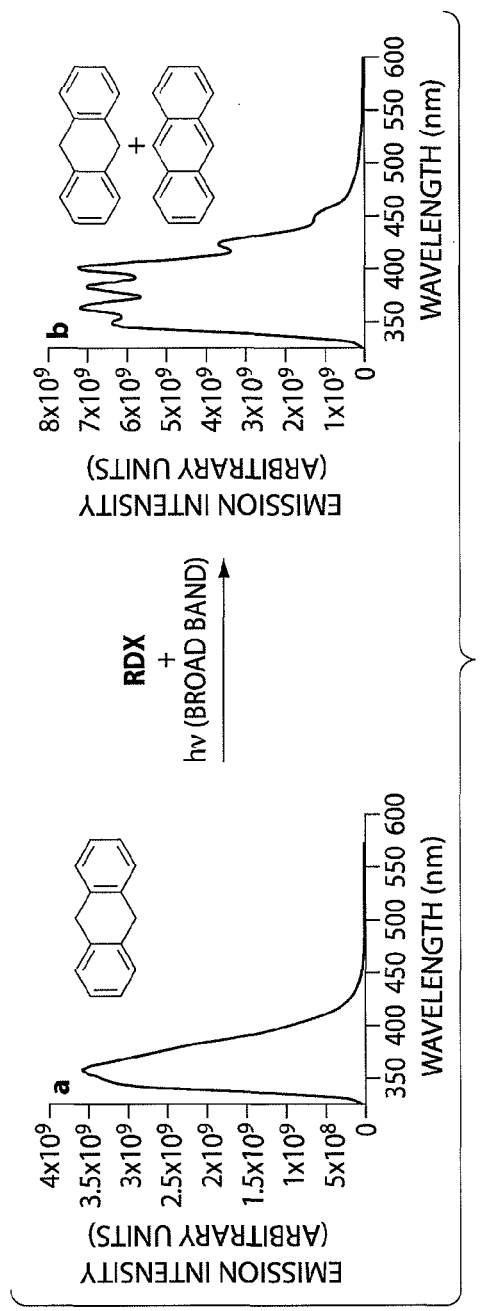
FIG. 5 shows fluorescence emission spectra of (a) 9,10-dihydroanthracene and (b) a mixture of anthracene and 9,10-dihydroanthracene, formed upon exposure of 9,10-dihydroanthracene to RDX and electromagnetic radiation.
Figure 6:
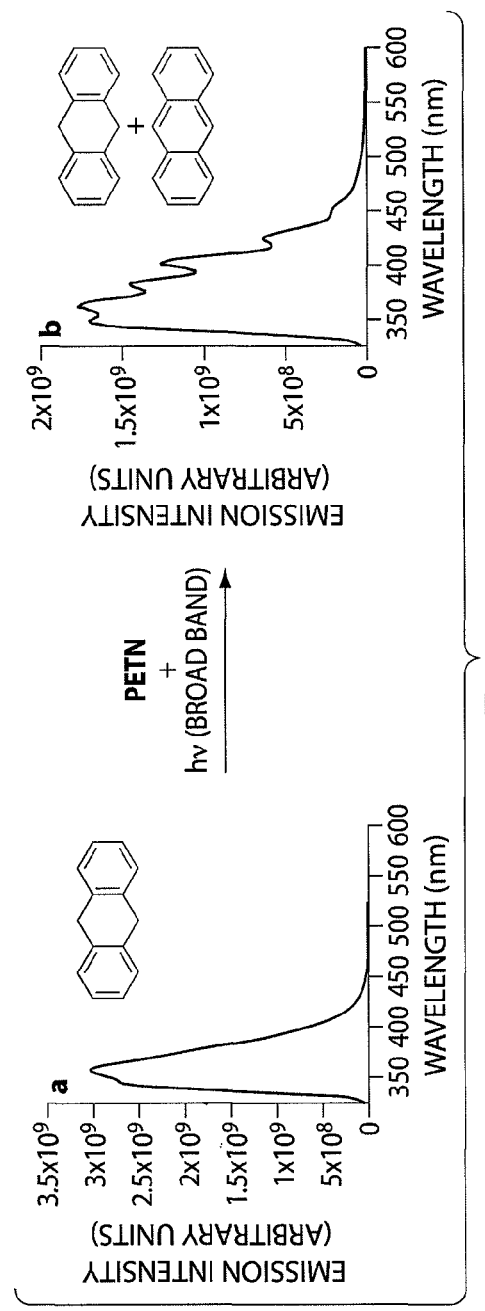
FIG. 6 shows fluorescence emission spectra of (a) 9,10-dihydroanthracene and (b) a mixture of anthracene and 9,10-dihydroanthracene, formed upon exposure of 9,10-dihydroanthracene to PETN and electromagnetic radiation.

The ability of 9,10-dihydro-10-methylacridine to interact with RDX via an electron-proton-electron transfer reaction was studied. The fluorescence emission spectrum of 9,10-dihydro-10-methylacridine was recorded and observed to have an emission maximum of 410 nm (FIG. 4A). The 9,10-dihydro-10-methylacridine was then exposed to RDX and irradiated with light (365 nm) for 30-50 seconds. The fluorescence emission spectrum of the irradiated sample was recorded (FIG. 5B). The emission maximum of the fluorescence emission was observed to shift from 410 nm to 490 nm, corresponding to the conversion of 9,10-dihydro-10-methylacridine to the corresponding acridinium salt.

Example 2

The ability of 9,10-dihydroanthracene to interact with RDX via an electron-proton-electron transfer reaction was studied. A solution of 9,10-dihydroanthracene in acetonitrile was sparged with argon prior to irradiation, and the fluorescence emission spectrum was recorded (FIG. 5A). A sample of RDX (424 μg RDX/mL, ca. 0.05 eq relative to dihydroanthracene) was added to the solution. The solution was irradiated with light (365 nm) from 30-50 seconds and the fluorescence emission spectrum was recorded (FIG. 5B). An observable change in the shape and intensity of the fluorescence emission was observed, corresponding to a mixture of anthracene and 9,10-dihydroanthracene.

Thus, the 9,10-dihydroanthracene was converted to anthracene upon exposure to RDX and irradiation with light.

Example 3

The ability of 9,10-dihydroanthracene to interact with PETN via an electron-proton-electron transfer reaction was studied. A solution of 9,10-dihydroanthracene in acetonitrile was sparged with argon prior to irradiation, and the fluorescence emission spectrum was recorded (FIG. 5A). A sample of PETN (533 μg PETN/mL, ca. 0.1 eq relative to dihydroacene) was added to the solution. The solution was irradiated with light (365 nm) from 30-50 seconds and the fluorescence emission spectrum was recorded (FIG. 5B). An observable change in the shape and intensity of the fluorescence emission was observed, corresponding to a mixture of anthracene and 9,10-dihydroanthracene.

Thus, the 9,10-dihydroanthracene was converted to anthracene upon exposure to PETN and irradiation with light.

Example 4

Figure 7:
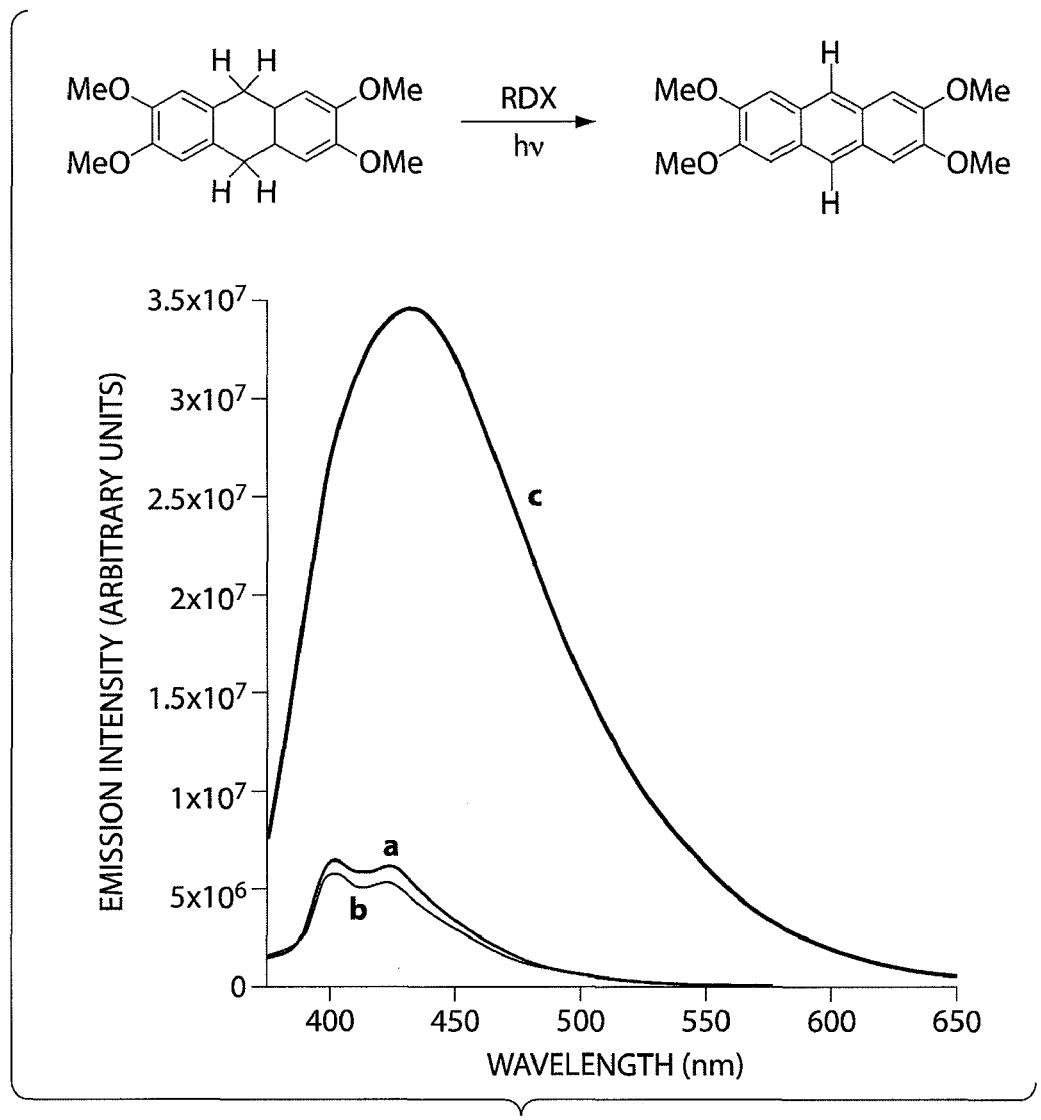
FIG. 7 shows fluorescence emission spectra of (a) 2,3,6,7,-tetramethoxy-9,10-dihydroanthracene, (b) 2,3,6,7,-tetramethoxy-9,10-dihydroanthracene upon irradiation with light (365 nm), and (c) 2,3,6,7,-tetramethoxy-anthracene, formed upon exposure of 2,3,6,7,-tetramethoxy-9,10-dihydroanthracene to RDX and irradiation with light (365 nm).

The ability of 2,3,6,7,-tetramethoxy-9,10-dihydroanthracene to interact with RDX via an electron-proton-electron transfer reaction was studied. The fluorescence emission spectrum of a solution of 2,3,6,7,-tetramethoxy-9,10-dihydroanthracene in acetonitrile was recorded (FIG. 7A), in the presence of oxygen. The solution was irradiated with light (365 nm) for 30 seconds and the fluorescence emission spectrum was recorded (FIG. 7B), showing relatively little change in the fluorescence emission. A sample of RDX (ca. 300 μg/mL RDX, 1.3 eq relative to the dihydroanthracene moiety) was then added to the solution. The solution was irradiated with light (365 nm) from 30-50 seconds and the fluorescence emission spectrum was recorded (FIG. 7C). A significant increase in fluorescence intensity was observed.

Thus, the conversion of 2,3,6,7,-tetramethoxy-9,10-dihydroanthracene to the corresponding acridinium salt does not proceed upon irradiation with light in the absence of RDX. However, 2,3,6,7,-tetramethoxy-9,10-dihydroanthracene was readily converted to the corresponding acridinium salt upon exposure to RDX and irradiation with light. This selective "turn-on" mechanism may be useful in the detection of analytes such as RDX.

Example 5

The ability of zinc complexes to interact with RDX via an electron-proton-electron transfer reaction was studied. A series of zinc complexes containing 9,10-dihydro-10-methylacridine ligands was exposed to RDX and irradiated with light (365 nm). Solutions of zinc complexes 10, 20, and 30 in acetonitrile were exposed to RDX, and the fluorescence spectra were recorded in the presence of oxygen.

Figure 8:
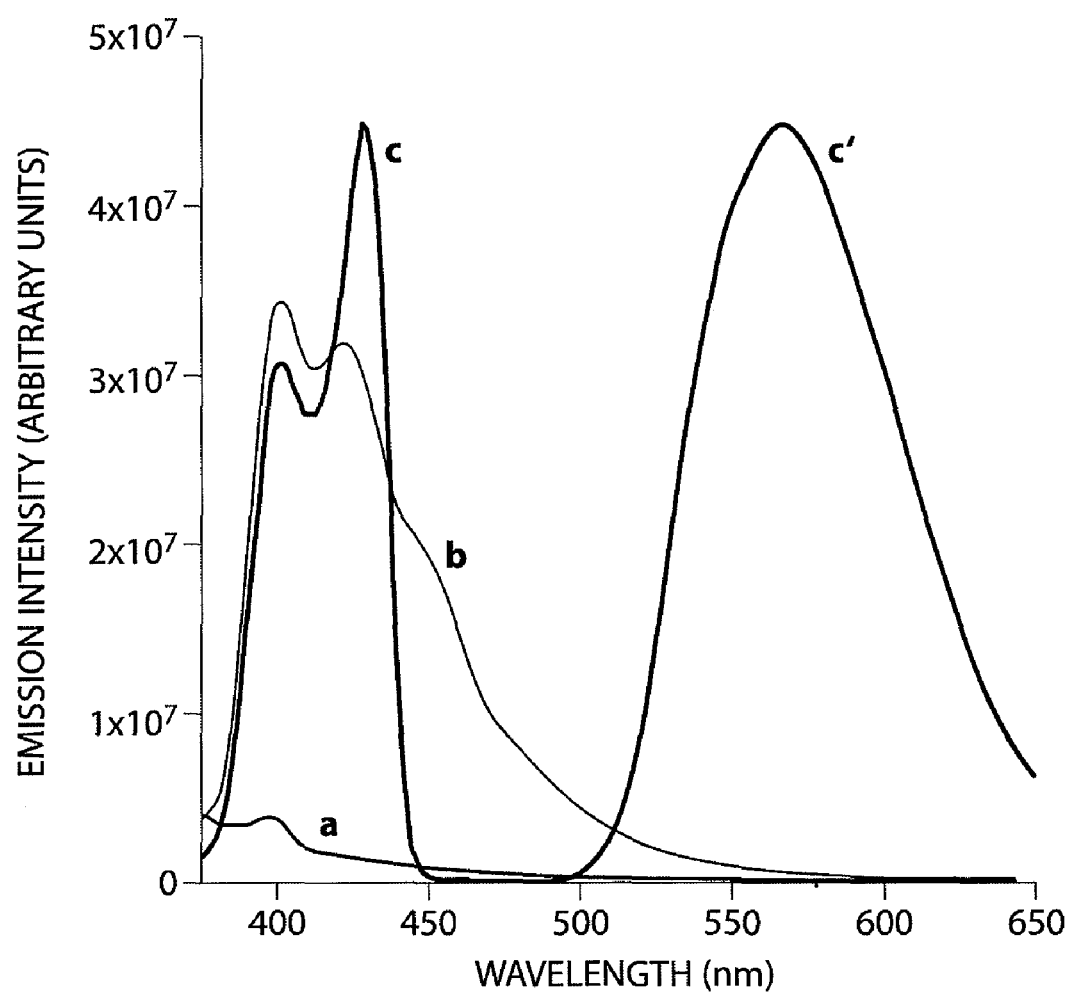
FIG. 8 shows the fluorescence emission spectra of (a) complex 10, (b) complex 10 upon irradiation with 365 nm light, and (c, c') the corresponding acridinium salt, formed upon exposure of complex 10 to RDX and irradiation with light (365 nm).

FIG. 8A shows the fluorescence emission spectra of complex 10, and FIG. 8B shows the fluorescence emission spectra of complex 10 upon irradiation with 365 nm light. A sample of RDX (330 μg/mL RDX, 2 eq relative to complex) was added to the solution and the solution was irradiated with light (365 nm) for 30-50 seconds. The fluorescence emission spectrum was recorded (FIG. 8C and FIG. 8C'), showing an observable change in wavelength and intensity of the fluorescence emission.

FIG. 9A shows the fluorescence emission spectra of complex 20, and FIG. 9B shows the fluorescence emission spectra of complex 10 upon irradiation with 365 nm light. A sample of RDX (304 μg/mL RDX, 11 eq relative to complex) was added to the solution and the solution was irradiated with light (365 nm) for 30-50 seconds. The fluorescence emission spectrum was recorded (FIG. 9C), showing an observable change in wavelength and intensity of the fluorescence emission.

FIG. 10A shows the fluorescence emission spectra of complex 20, and FIG. 10B shows the fluorescence emission spectra of complex 10 upon irradiation with 365 nm light. A sample of RDX (67 μg/mL RDX, 5 eq relative to complex) was added to the solution and the solution was irradiated with light (365 nm) for 30-50 seconds. The fluorescence emission spectrum was recorded (FIG. 10C), showing an observable change in wavelength and intensity of the fluorescence emission.

Example 6

Figure 11:
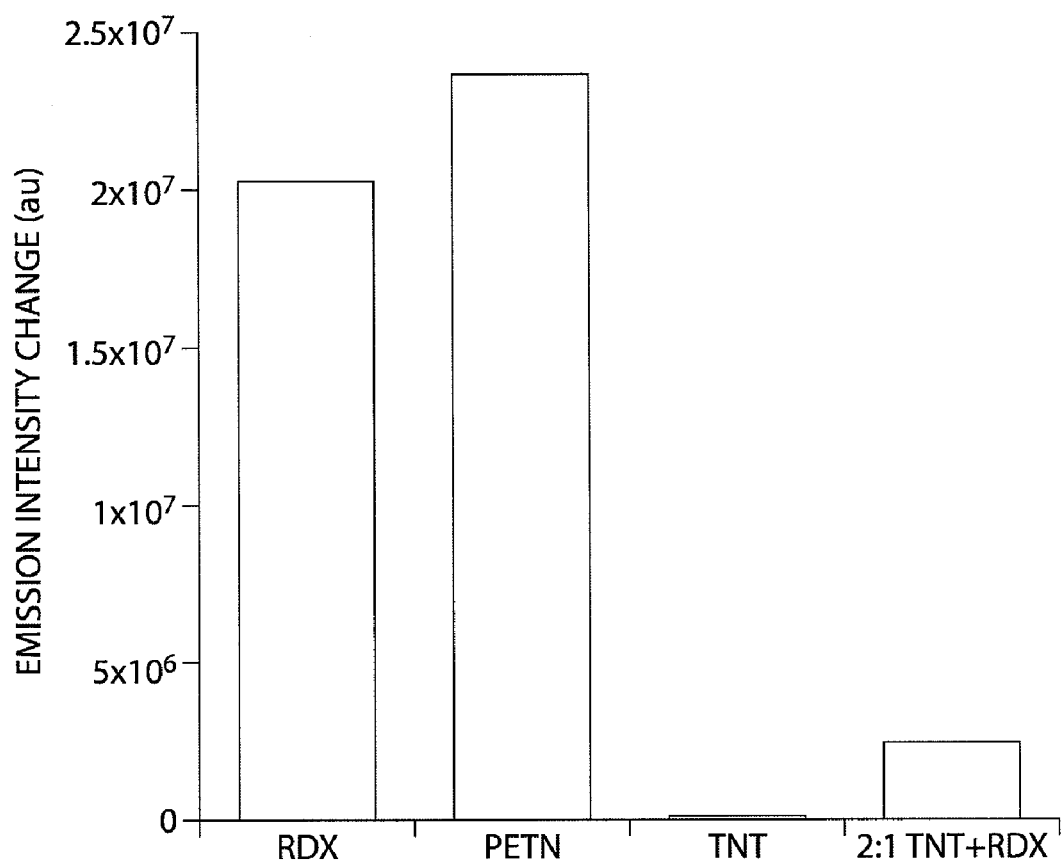
FIG. 11 shows a graph of the change in the fluorescence emission intensity of complex 10 at 550 nm, upon exposure to various analytes.

The response of a zinc complex to a series of analytes was then observed. Solutions of zinc complex 10 in acetonitrile were exposed to approximately 0.001M samples of various analytes, including RDX, PETN, TNT, and a 2:1 mixture of TNT and RDX. The solutions were irradiated with 365 nm light for 30 seconds, and the fluorescence emission spectra were recorded. FIG. 11 shows a graph of the change in the fluorescence emission intensity of complex 10 at 550 nm, upon exposure to each analyte.

As shown in FIG. 11, complex 10 exhibited large changes in emission intensity when exposed to RDX and PETN, indicating that complex 10 undergoes a rapid electron-proton-electron transfer reaction with RDX and PETN.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A sensor, comprising:
a sample cell comprising a solution or a support material containing a compound comprising the structure,

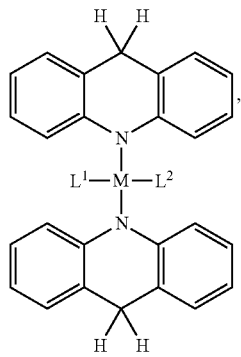

wherein M is a metal, and $L^1$ and $L^2$ can be the same or different and are halide, hydroxy, amine, a carbonyl group, alkyl, heteroalkyl, aryl, heteroaryl, or substituted derivatives thereof, or $L^1$ and $L^2$ are joined together to form a bidentate ligand,
a source of energy directed onto the sample cell to cause an emission of radiation; and
an emission detector positioned to detect the emission from said sample cell.

2. A sensor as in claim 1, wherein M is Co or Zn.

3. A sensor as in claim 1, wherein M is Zn.

4. A sensor as in claim 1, wherein $L^1$ and $L^2$ are halide, methanol, or $L^1$ and $L^2$ are joined together to form ethylenediamine or a substituted derivative thereof.

5. A sensor as in claim 1, wherein $L^1$ and $L^2$ are joined together to form a ligand having the structure,

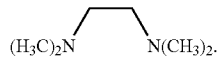

6. A sensor as in claim 1, wherein the compound is in solution.

7. A sensor as in claim 1, wherein the compound is dispersed within the support material.

8. A sensor as in claim 7, wherein the support material is a polymer.

9. A sensor as in claim 8, wherein the polymer is poly(methyl methacrylate), polyethylene, polypropylene, poly(vinyl chloride), poly(vinyl benzoate), poly(vinyl acetate), cellulose, corn starch, poly(vinyl pyrrolidinone), polyacrylamide, epoxy, silicone, poly(vinyl butyral), polyurethane, nylon, polacetal, polycarbonate, polyester, polyether, polybutadiene, or combinations thereof.

10. A sensor as in claim 8, wherein the polymer is poly(methylmethacrylate), poly(vinylpyrrolidinone), or poly(4-vinylpyridine).

11. A sensor as in claim 8, wherein the polymer is poly(methylmethacrylate).

12. A sensor as in claim 8, wherein the polymer is poly(vinylpyrrolidinone).

13. A sensor as in claim 1, wherein said source of energy directed onto the sample cell causes the compound to transfer an electron to an analyte.

14. A sensor as in claim 1, wherein the source of energy, when applied to the compound, causes an emission of radiation and causes the compound to transfer an electron to an analyte.

15. A sensor as in claim 1, wherein the source of energy is an electric, magnetic, optical, acoustic, electromagnetic, or mechanical field.

16. A sensor as in claim 1, wherein the source of energy is electromagnetic radiation.

* * * * *

UNITED STATES PATENT AND TRADEMARK OFFICE
CERTIFICATE OF CORRECTION

PATENT NO.         : 7,862,775 B2                                    Page 1 of 1
APPLICATION NO.    : 12/693868
DATED              : January 4, 2011
INVENTOR(S)        : Timothy M. Swager et al.

It is certified that error appears in the above-identified patent and that said Letters Patent is hereby corrected as shown below:

At column 1, lines 18-21, "This invention was made with government support under grant number DAAD19-02-D-0002 awarded by the Army Research Office. The government has certain rights in the invention." should be -- This invention was made with government support under grant number DAAD19-02-D-0002 awarded by the Army and grant number HR0011-06-P-0036 awarded by the Defense Advanced Research Projects Agency. The government has certain rights in this invention. --.

Signed and Sealed this
Twenty-fourth Day of May, 2011

David J. Kappos
*Director of the United States Patent and Trademark Office*